United States Patent [19]

Dubousset

[11] Patent Number: 5,147,360
[45] Date of Patent: Sep. 15, 1992

[54] OSTEOSYNTHESIS DEVICE FOR THE CORRECTION OF SPINAL CURVATURES

[75] Inventor: Jean Dubousset, Clamart, France

[73] Assignee: Societe de Fabrication de Materiel Orthopedique, Paris, France

[21] Appl. No.: 656,822

[22] Filed: Feb. 19, 1991

[30] Foreign Application Priority Data

Feb. 19, 1990 [FR] France .................. 9001970

[51] Int. Cl.⁵ .......................................... A61B 17/56
[52] U.S. Cl. .............................. 606/61; 606/72
[58] Field of Search ............... 606/53, 54, 60, 61, 606/62, 69–73

[56] References Cited

U.S. PATENT DOCUMENTS

| | | | |
|---|---|---|---|
| 4,047,524 | 9/1977 | Hall | 606/61 |
| 4,289,123 | 9/1981 | Dunn | 606/61 |
| 4,773,402 | 9/1988 | Asher | 606/61 |
| 4,827,918 | 5/1989 | Olerud | 606/61 |
| 5,000,165 | 3/1991 | Watanabe | 606/61 |
| 5,002,542 | 3/1991 | Frigg | 606/61 |

FOREIGN PATENT DOCUMENTS

| | | |
|---|---|---|
| 0128058 | 12/1984 | European Pat. Off. |
| 0348272 | 12/1989 | European Pat. Off. |
| 2615095 | 11/1988 | France .................. 606/61 |
| 392927 | 10/1990 | France .................. 606/61 |
| 2645427 | 10/1990 | France .................. 606/61 |
| 1516105 | 10/1989 | U.S.S.R. .................. 606/72 |
| 9004948 | 5/1990 | World Int. Prop. O. .......... 606/61 |

*Primary Examiner*—Robert A. Hafer
*Assistant Examiner*—David J. Kenealy
*Attorney, Agent, or Firm*—Wenderoth, Lind & Ponack

[57] ABSTRACT

An osteosynthesis spinal device comprises two rods (1, 2), anterior and posterior rods, respectively. Plates (4) for fixation of the anterior rod (1) to the extreme vertebral bodies, for example T12 and L3, have an arched surface corresponding to the anterolateral anatomy of the vertebral bodies. The plates (4) are equipped with screws (14) for locking the rod (1) and screws (5) of the cancellous bone type. Screws (3) ensure the osseous anchoring of the posterior rod (2) and bars (6) for transverse connection of the rods (1 and 2) constitute with the rods, a rigid frame assembly. The anterior rod (1) reinforces the stability and the rigidity of the assembly and is advantageously embedded in a furrow (30) made in the vertebral bodies which is subsequently covered with the periostrum.

18 Claims, 8 Drawing Sheets

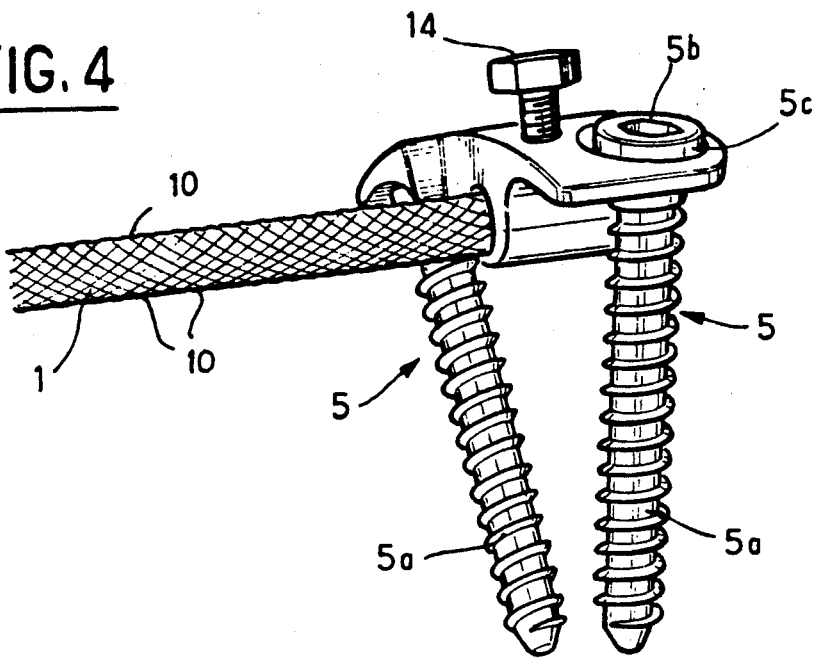
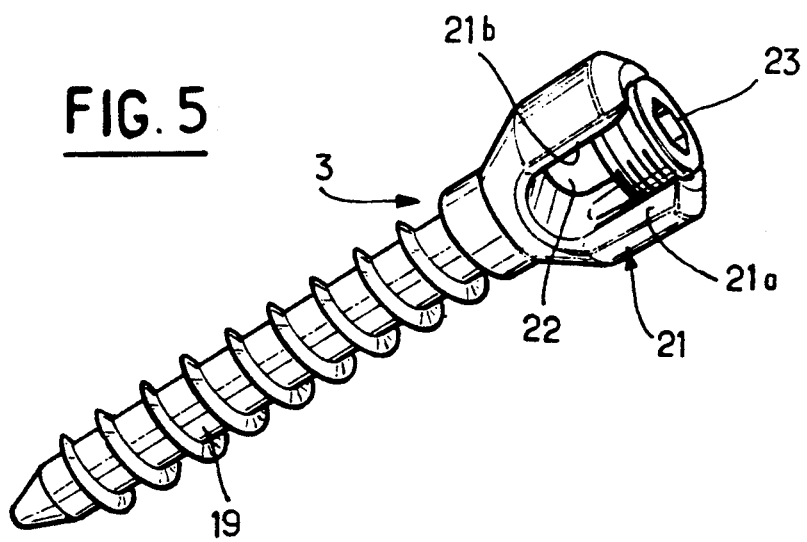

OSTEOSYNTHESIS DEVICE FOR THE CORRECTION OF SPINAL CURVATURES

BACKGROUND OF THE INVENTION

The present invention relates to a plate for an osteosynthesis device for correction of spinal curvatures, as well as to a device incorporating this plate. The plate is intended to ensure the fixation of a rod extending over the anterior part of the vertebral bodies or connected vertebrae.

It is known that the anterior approach to the thoracolumbar spine is used in the following cases:

In traumatology, in the case of a comminuted fracture. This maximum instability of the spine does in fact make an anterior support obligatory.

In neurosurgery, the ablation of the vertebral body, on system be connected to the graft.

In spinal curvatures, certain curvatures involving marked rotation, especially in the lumbar region, necessitate an anterior approach in order to restore better lordosis. It is a question either of correcting and maintaining scoliosis or of treating kyphosis. In the latter case, the kyphosis may be of a large radius of curvature and harmonious, or in contrast very short (angular kyphosis).

As regards these short kyphoses, several aetiologies may be singled out, among which there may be mentioned in particular congenital deformations (hemivertebrae), infections (Pott's disease), recent traumatisms (comminuted fractures of the vertebral body) or earlier traumatisms, and benign tumors or especially malignant tumors (metastases). In the case of a tumour reaching the vertebral body, even in the absence of kyphosis the anterior approach is justified.

Of the designs known, two types of devices permitting the anterior approach are singled out here:

a) systems permitting distraction, or compression by means of threaded rods and bolts, and b) plates.

The distraction systems are derived from known instrumentation used in the treatment of scolioses. Their principle is always the same: one or two screws are fixed on the vertebral body of the vertebrae, and they are connected via one or two rods making it possible to perform distraction, that is to say extension, of the vertebrae, and thereby to correct the kyphosis. Then, once these rods are fixed to the screws, the assembly between the vertebral bodies is stabilized. These systems have the advantage of permitting distraction or compression, but they are not sufficiently stable with one rod alone, or are too bulky with two rods. Nor do some of these known designs permit derotation, and they present vascular risks as well as risks of pseudarthroses In addition, angular losses are also observed.

The plates are fixed to the vertebral bodies by means of two or three screws. They have the advantage of projecting less and of usually being stronger than the rod systems. On the other hand, their use does not permit direct distraction, and thus instrumental correction of the kyphosis or the scoliosis.

SUMMARY OF THE INVENTION

The aim of the invention is therefore to provide a device for osteosynthesis by the anterior approach, which, once in position, presents minimal projections relative to the vertebrae, in particular anteriorly, in order to avoid any contact with the vessels, such as the aorta and the vena cava, which permits effective correction of the spinal curvatures with good mechanical stability over time and under repeated stress, and finally whose positioning by the surgeon is as simple as possible.

A plate for an osteosynthesis device, according to the invention, is incurved and has an arched outer surface corresponding to the anterolateral anatomy of the vertebral. It comprises on its inner face, opposite the arched outer surface, a boss drilled with an opening for the passage of the rod a means is provided for joining the plate and the rod, and two bores are drilled in the plate in order to receive, in each case, a screw for fixation of the plate to the vertebral body.

According to one feature of the invention, at least the most anterior bore of the plate is bevelled for the purpose of receiving a screw provided with a conical head matching the bevel in order to permit an orientation of the screw in the vertebral body and to prevent any projection of the head of the screw.

The two bores have a caudal or cranial orientation and are offset in a sagittal plane.

According to another characteristic of the invention the bores are made in the vicinity of the ends of the plate, and the means for joining the plate and the rod comprise a tapped hole connecting the arched outer surface to the hole of the boss, and a screw adapted so as to be screwed into this tapped hole.

The osteosynthesis device according to the invention comprises in combination:

two rods intended to be fixed respectively on an anterior part and on a lateral or posterior part of the vertebral bodies, means for fixation of the lateral or posterior rod to the vertebrae, plates whose bosses can be passed through by the opposite ends of the anterior rod, means for locking at least the anterior rod in the plates, and means for anchoring the plates in the vertebral bodies of the connected vertebrae.

According to other characteristics of the invention, the device comprises means for rigid transverse connection of the two rods to each other, constituting with the latter a rigid frame assembly.

The means for rigid transverse connection of the rods are rigid bars, each equipped with two terminal hooks delimiting grooves for receiving the rods, as well as members for locking the rods in the grooves of the hooks.

The means for fixation of the lateral or posterior rod are screws of the type comprising a U-shaped body and a threaded plug for locking the rod in the body, which can be screwed inside the U-shaped body on tappings in its lateral branches.

This osteosynthesis device for anterior correction is indicated most particularly for lumbar, thoracolumbar and thoracic scolioses. It may involve several levels. The rods are preferably of the roughened-surface type, and the lateral or posterior rod is arched and, by derotation, provides the three-dimensional correction of the spinal segment operated on.

The invention will now be described below with reference to the attached drawings which illustrate several embodiments thereof by way of non-limiting examples.

BRIEF DESCRIPTION OF THE DRAWINGS

FIG. 4 is a perspective view of the plate of FIGS. 2 and 3, provided with the two screws and having an anterior rod passing therethrough and locked by means of a third screw fitting in the plate.

FIG. 5 is a perspective view, on an enlarged scale, of one of the screws for osseous anchoring of the lateral or posterior rod of the device in FIG. 1.

DETAILED DESCRIPTION OF THE PREFERRED EMBODIMENT

Figure 1:
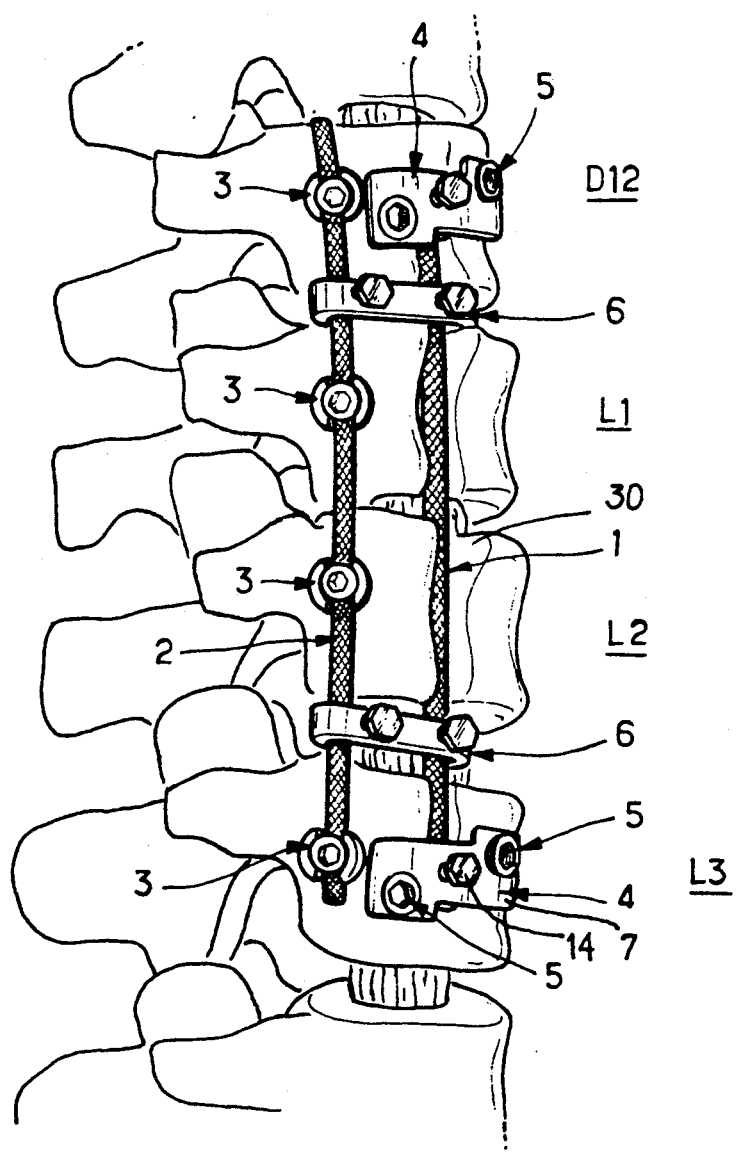
FIG. 1 is a side elevation view of a spinal provided with an osteosynthesis device according to the invention.

The osteosynthesis device as shown in FIG. 1 is intended for the correction of spinal curvatures in a thoracolumbar segment comprising, for example, four vertebrae T12, L1, L2, L3.

The device comprises the following elements:

two rods 1 and 2 intended to be fixed, respectively, on an anterior part and on a lateral or posterior part of the vertebral bodies, means for fixation of the lateral or posterior rod 2 to the vertebrae, comprising, in the example shown, screws 3 for osseous anchoring, which are four in number and are distributed from one end to the other of the rod 2, two plates 4 designed to permit the fixation of the anterior rod 1 to the vertebral bodies of the vertebrae T12-L3, means for locking the anterior rod 1 in the plates 4, as well as means for anchoring the plates 4 in the vertebral bodies, comprising, in the example described, two screws 5 of cancellous bone passing through each plate 4, and members 6 for rigid transverse connection of the two rods 1 and 2 to each other, constituting, with the latter, a rigid frame assembly.

The rods 1 and 2 are preferably knurled over their whole length and are made, for example, of reinforced steel. They can be of different sizes depending on the number of levels operated on, and their diameters may be, for example, 4 mm. In the event of an anterior approach to the spinal segment, one of the two rods 1 and 2 has the function of correcting the segment (posterior rod 2), and the other (anterior rod 1) stabilizes the assembly and gives it its overall rigidity.

Each plate 4 is incurved and has an arched outer surface 7 corresponding to the anterolateral anatomy of the vertebral bodies. On its inner face, opposite the outer surface 7, it comprises a boss 8 in the median area drilled with a hole 9 for passage of the anterior rod 1. Two bores 11 and 12 are, moreover drilled in each plate 4 in the vicinity of its ends, these bores being adapted in order to receive in each case a screw 5 of the cancellous bone type. The screws 5 comprise threaded rod 5a for cancellous bone a head 5b (FIG. 4) recessed with a hexagonal hole permitting the tightening of the screw. At least the most anterior bore 12 has a bevel which can co-operate with a conical surface 5c of the head 5b, this making it possible to orientate the screw 5 in the vertebral body of the vertebra (T12, L3). The second bore 11 can also have a bevel 11a similar to the conical bevel 12a.

These two bores 11 and 12 can have, for example, a caudal orientation if they affect the subjacent vertebra and, for example, a cranial orientation if they affect the suprajacent vertebra. They are offset in a sagittal plane in order to prevent any interference between the two fixation screws 5 and in order to increase the stability of the anchoring.

A tapped hole 13 is made in each plate 4 perpendicular to the axis of the passage hole 9 and connects the arched surface 7 to the hole 9. A screw 14 (FIG. 4) can be screwed into the hole 13 in order to lock the rod 1 in translation and in rotation relative to the plate 4.

The rigid members 6 for connection of the rods 1 and 2 are two in number. Each member 6 comprises a bar equipped with two terminal hooks 15 delimiting grooves 16 for receiving the corresponding rods 1 and 2. Also formed in each bar 6, in the vicinity of the hooks 16, are two threaded holes 17 into which there may be screwed the threaded rods of hexagonal-headed screws 18, these screws 18 making it possible to lock the rods 1 and 2 in the grooves 16.

The rigid bars 6 for transverse connection can be, for example, of the type described in French Patent Application 89/04,750 filed on Apr. 11, 1989 by the Applicant.

The means for fixation of the lateral or posterior rod 2 are, in the example described, screws 3 for osseous anchoring, comprising a threaded rod 19 and a U-shaped body 21 presenting a channel 22 delimited by two lateral branches 21a and 21b of the body 21. The knurled rod 2 can come to rest in the channel 22, where it is locked in translation and in rotation by a threaded plug 23. The plug 23 is screwed inside the body 21 on tappings in its lateral branches 21a and 21b, and the face of the plug 23 orientated towards the rod 2 can be provided with an anchoring means such as a central tip sinking into the surface of the rod.

The screw 3 is, advantageously, in accordance with described in French Patent Application 88/08,538 filed on Jun. 24, 1988 by the Applicant.

The screws 3 are placed in the posterior part of the vertebral bodies and ensure, by means of the fixation of the plug 23, the immobilization of the posterior rod 2 on the screws 3.

The two rods 1 and 2 have knurled notches 10 (FIG. 4) which can co-operate with needles of the screws 14 in order to lock the rods.

The operating technique for the positioning of the spinal correction device which has just been described is as follows (FIGS. 7 to 11).

Figure 11:
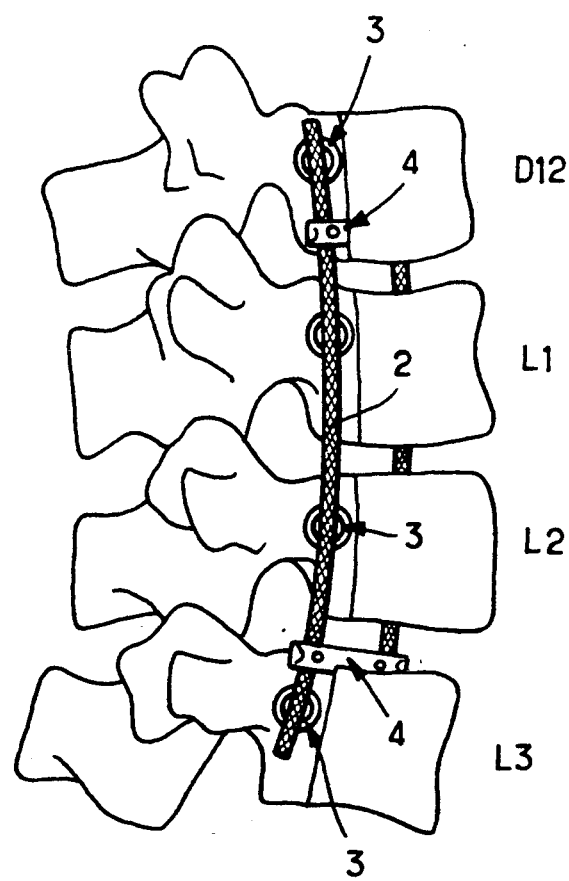
FIGS. 7 to 11 are elevation views illustrating the operating sequence involved in the positioning, by a surgeon, of the correction device in FIGS. 1 to 6 on a corresponding spinal segment.
Figure 8:
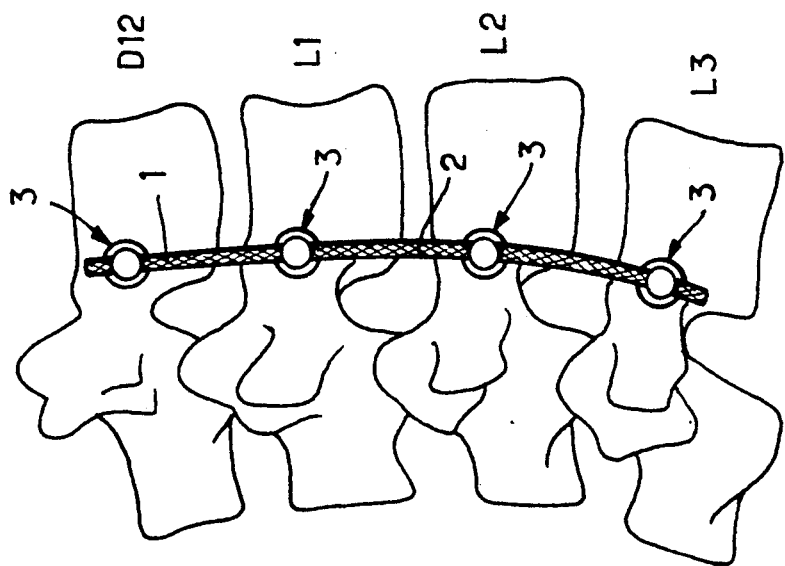
Figure 7:
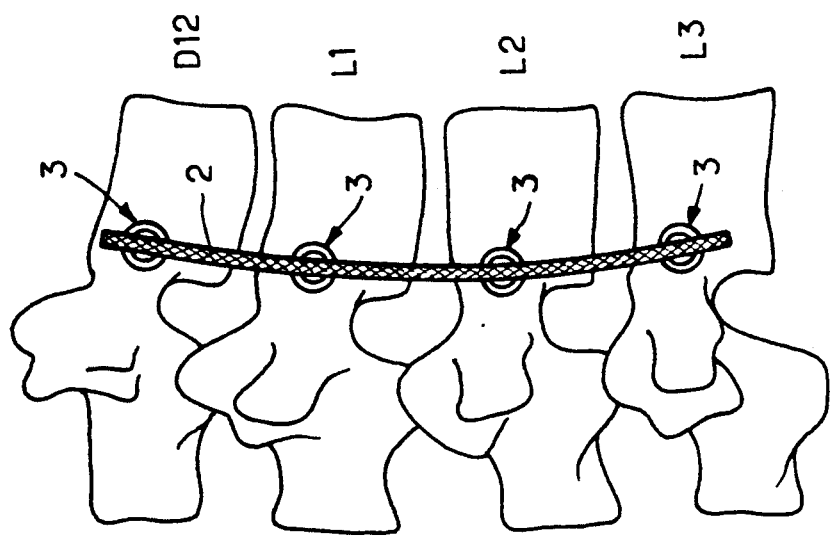
Figure 10:
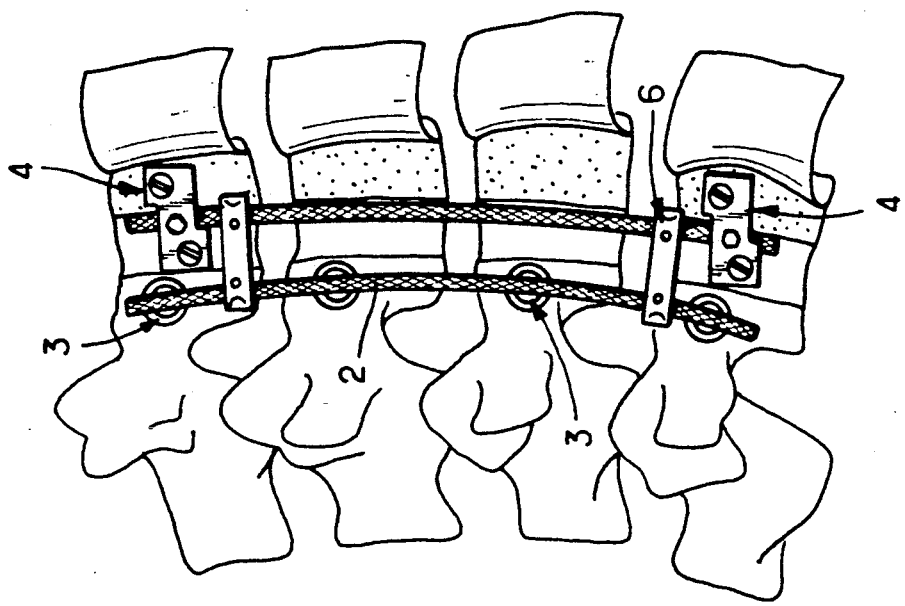
Figure 9:
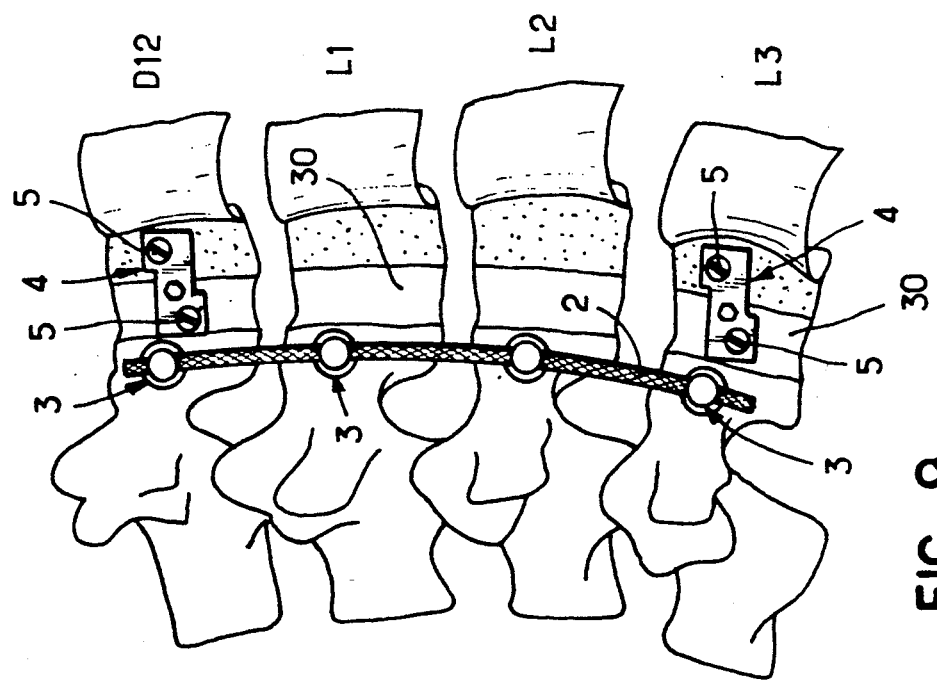

FIG. 7 shows a thoracolumbar section T12-L1-L2-L3 which is similar to that in FIG. 1 and which presents kyphosis:

a) Screws 3 for plugs 23 are positioned on the posterior part of the vertebral bodies.

b) Arching of the posterior rod 2 is carried out, and it is positioned in the channels or grooves 22 of the screws 3 (FIG. 7).

c) The surgeon performs derotation of the rod 2 and correction of the kyphosis (FIG. 8), after which he positions the threaded plugs 23 in the bodies 21 of the screws 3.

d) The surgeon carries out removal of the periosteum from the lateral part of the vertebral bodies of vertebrae T12 to L3. The surgeon thus forms a furrow 30 on the anterolateral part of the vertebral bodies operated on (FIG. 9).

e) The surgeon positions the two plates 4 on the extreme vertebrae T12 and L3 and fixes them in the vertebral bodies by inserting into them the two bone screws 5 (FIG. 9).

f) The surgeon performs arching of the anterior rod 1 and positions it in the passage holes 9 of the two plates 4 (FIG. 10). He then carries out distraction of the two plates 4. The surgeon locks the rod 1 in translation and in rotation in the plates 4 by means of the screws 14, then the rod 1 is definitively fixed in the plates 4 by breaking the hexagonal heads of the screws 14 (FIG. 10).

g) The surgeon positions the bars 6 for transverse fixation and rigid connection of the anterior rod 1 and the posterior rod 2, which are definitively fixed in the bars 6 by breaking the heads of the screws 18.

h) And finally, the surgeon replaces the periosteum in order to plug the furrow 30, the spinal segment in question finally having the appearance as shown in FIG. 11.

In addition to those mentioned above, the invention has the following advantages:

The assembly is designed as a rectangular frame, by virtue of the rigid bars 6 for transverse fixation, which confers upon the assembly great strength and great stability.

The positioning of the correction device is modular, element by element.

The anterior rod 1 is buried in the furrow 30 inside the vertebral bodies, which prevents any contact with the large vessels. Similarly, the bevels 11a and 12a of the plates 4 and the complementary conical heads 5c of the screws 5 allow these heads to be driven almost completely into the plates 4.

The knurled notches 10 of the rods 1 and 2 ensure a firm fixation of the latter to the plates 4 and to the screws 3.

Figure 12:
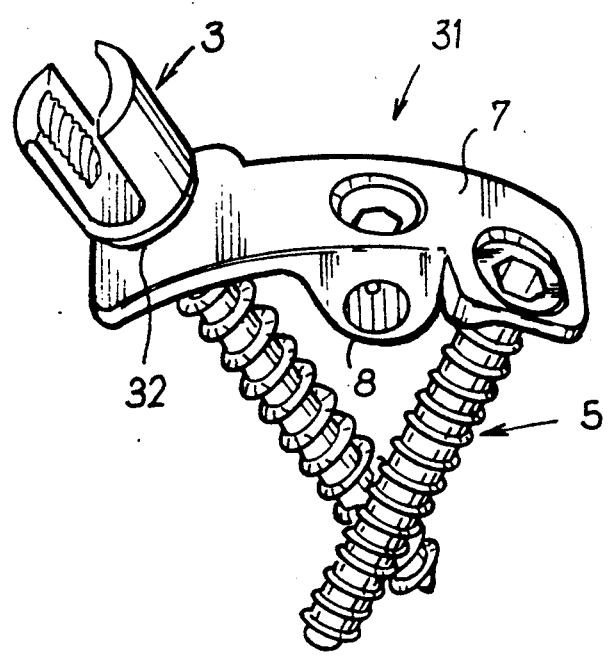
FIG. 12 is a perspective view of a second embodiment of the plate of a device of FIG. 1 and of the screws fitting this plate.

In its second embodiment illustrated in FIG. 12, a plate 31 extends over a sufficient length for a lateral or posterior bore 32 to receive a screw 3, in this case fulfilling a double function: on the one hand, the function of fixing the plate 31 to the vertebral body and, on the other hand, the function of fixing the lateral or posterior rod 2 to the plate 31. The screw 3 can be, for example, of the type as described above (FIG. 5) with a U-shaped body 21 and a threaded plug 23.

The use of the plates 31 thus makes it possible to omit a screw 5 in the assembly in FIG. 1.

Figure 13:
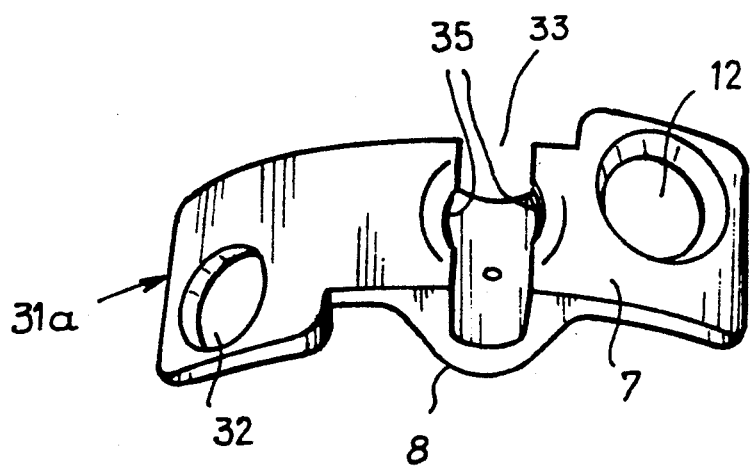
FIG. 13 is a perspective view of an alternative embodiment of the plate in FIG. 12.

FIG. 13 shows an alternative embodiment 31a of the plate 31, from which it differs in that the opening of the boss 8 is here a longitudinal channel 33, open on the arched outer surface 7, which is thus interrupted on each side of the channel 33 in order to permit the insertion therein of the anterior rod 1. The plate 31a is completed with a means for locking the rod 1 in the channel 33, it being possible, for example, for a bolt 34 (FIG. 14) to be screwed into tappings 35 machined on the edges of the channel 33.

Figure 14:
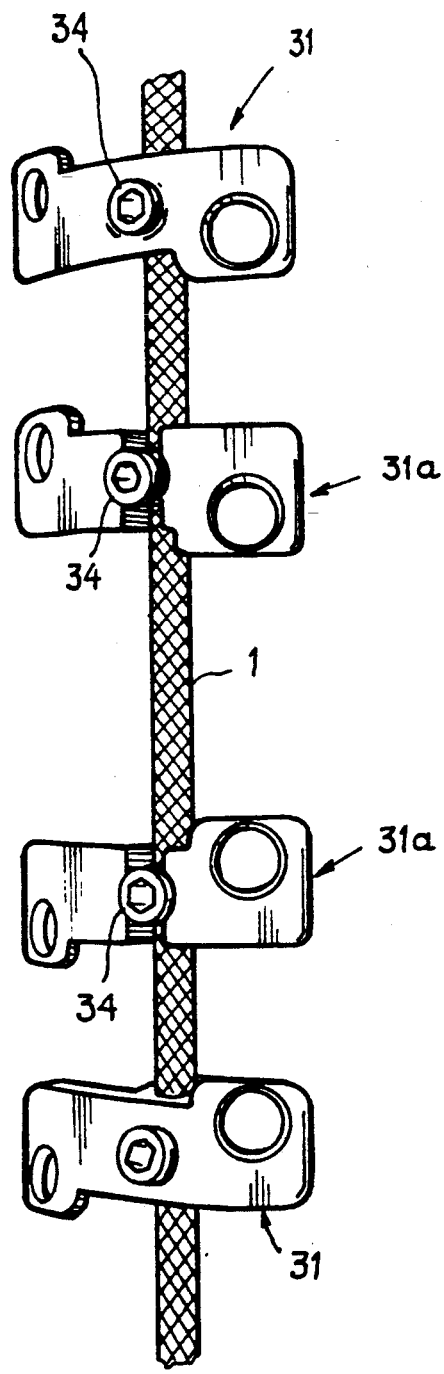
FIG. 14 is an elevation view of an osteosynthesis device according to the invention, comprising several plates according to FIGS. 11 and 12.

FIG. 14 illustrates an exemplary embodiment of the osteosynthesis device with plates 31 and 31a: at its ends the device comprises two plates 31, the anterior rod 1 passing through the bosses 8 and being locked in the latter by means of bolts 34 (or 14 as in FIG. 1), while the lateral rod 2 (not shown) is fixed by means of two screws 3 on the terminal plates 31. The device is completed by plates 31a, here two in number, which are arranged between the plates 31 in order to ensure a rigid transverse connection of the rods 1, 2 to each other, the anterior rod 1 being locked in the channels 33 by the bolts 34.

Figure 2:
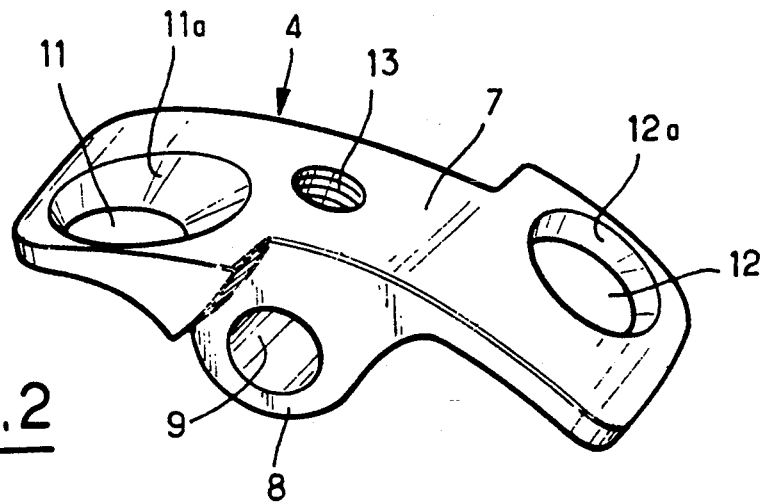
FIG. 2 is a perspective view, on an enlarged scale, of one of the plates of the osteosynthesis device in FIG. 1.
Figure 3:
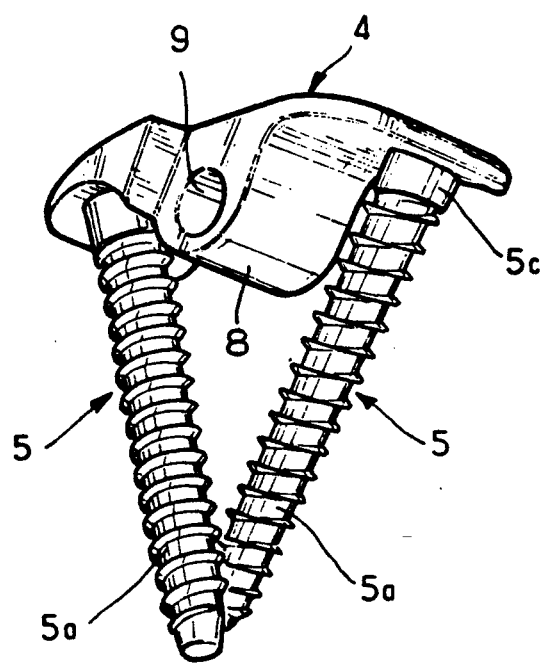
FIG. 3 is a perspective view, at a different angle, of the plate in FIG. 2 and of two screws fitting the plate.
Figure 6:
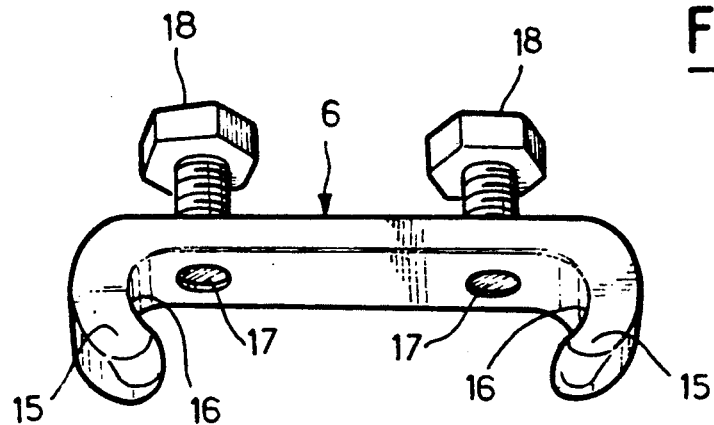
FIG. 6 is a perspective view of an element for rigid transverse connection of the two rods of the device in FIG. 1.

It should be noted that, as an alternative, it is possible for the intermediate plates 31a not to be of the type in FIG. 11, but of the type in FIG. 2. In this case the intermediate plates do not ensure the rigid transverse connection of the rods to each other, it being possible for this connection to be ensured by bars such as has 6.

Finally, the different plates 4, 31 and 31a described can have small points (not visible in the drawings) on their faces opposite the arched outer surface 7, in order to facilitate the anchoring of the plate on the vertebra as well as the positioning of the equipment by the surgeon. It is also possible to use, between the terminal plates 4 or 31, elongate plates 31a and devices for transverse connection, such as bars 6. The rods 1 and 2 can be designed in accordance with European Patent 0,128,058, and the rigid connection members can be of a number greater than two, depending on the number of levels operated on. In some cases the device can be without intermediate members for transverse connection between the rods, this rigid connection then being provided by the elongate terminal plates 31 or, optionally, 31a.

I claim:

1. A plate for an osteosynthesis device for the correction of spinal curvatures for fixing a rod extending over the anterior portion of the vertebral bodies of connected vertebrae, the plate having the shape of the inward curve with an arched convex outer surface, said arched convex outer surface corresponding to the anterolateral anatomy of the vertebral bodies, and an inner surface opposite said arched convex outer surface having a boss protruding from said inner surface in a median area of the plate in a direction away from said arched convex outer surface, said boss having an opening extending therethrough for receiving the rod, said plate further comprising means for joining the rod thereto and two bores extending through the plate for receiving respective fixation screws for fixing the plate to a vertebral body.

2. The plate of claim 1, wherein at least the most anterior said bore in said plate is bevelled for receiving a screw having a conical head matching the bevel of said bore end in order to orient the screw in a vertebral body.

3. The plate of claim 1, wherein said inner surface opposite said arched convex outer surface has small points thereon for anchoring the plate on a vertebra.

4. The plate of claim 1, wherein said bores are located in the vicinity of the ends of the plate and said means for joining the rod to the plate comprises a tapped hole connecting said arched outer surface to said opening of said boss and a screw adapted to be screwed into said tapped holed.

5. The plate of claim 1, wherein one of said bores is a lateral or posterior bore and the plate has a sufficient length for said lateral or posterior bore to be able to fix a lateral or posterior rod to the plate with a screw in sad lateral or posterior bore.

6. The plate of claim 1, wherein said opening of said boss is a channel therein open on said arched outer surface for permitting the insertion of an anterior rod, said means for joining the rod to the plate comprising tapping son the edges of said channel and a bolt adapted to be screwed into said tappings.

7. An osteosynthesis device for the correction of spinal curvatures, comprising:
  a first rod to be fixed on the anterior part of the vertebral bodies and a second rod to be fixed on the lateral or posterior part of the vertebral bodies;
  means for fixing said second rod to the lateral or posterior part of the vertebral bodies;
  a plurality of plates, each said plate having shape of an inward curve with an arched convex outer surface, said arched convex outer surface corresponding to the anterolatral anatomy of the vertebral bodies, and an inner surface opposite said arched convex outer surface having a boss protruding from said inner surface in a median area of said plate in a direction away from said arched convex outer surface, said boss having an opening extending therethrough for receiving said first rod;
  means for locking said first rod in said plates; and
  means for anchoring said plates in the vertebral bodies.

8. The osteosynthesis device of claim 7, said device including means for rigidly transversely connecting said first and second rods to each other so as to form a rigid frame assembly.

9. The osteosynthesis device of claim 8, wherein said means for rigidly transversely connecting said first and second rods to each other comprises rigid bars, each said rigid bar having two terminal hooks defining grooves for receiving said rods, and members for locking said rods in said grooves of said terminal hooks.

10. The osteosynthesis device of claim 7, wherein said means for anchoring said plates in the vertebral bodies comprises two bores extending through each said plate and fixation screws to be received in respective said bores, said bores having bevels therein and said screws have control heads corresponding to said bevels so as to prevent projection of said heads of said screws relative to said arched outer surfaces of said plates.

11. The osteosynthesis device of claim 7, wherein said means for fixing said second rod to the lateral or posterior part of the vertebral bodies comprises screws having a U-shaped body having lateral branches that are tapped and a threaded plug for locking said second rod in said U-shaped body by being screwed into said lateral branches of said U-shaped body.

12. The osteosynthesis device of claim 7, wherein two said plates are provided at ends of said device, the two said plates each having a lateral or posterior said bore and each having a length sufficient for said lateral or posterior bore to fix said second rod to said plate with a screw in said lateral or posterior bore, further said plates being provided between the two said plates.

13. The osteosynthesis device of claim 12, wherein the further said plates also each have a lateral or posterior said bore and a length sufficient for said lateral or posterior bore to fix said second rod to said plate with a screw in said lateral or posterior bore.

14. The osteosynthesis device of claim 12, wherein said opening of said boss of each of the further said plates is a channel therein open on said arched outer surface permitting the insertion of said first rod, said means for locking said first rod in said plates comprising tapping son the edges of said channel and a bolt adapted to be screwed into said tappings.

15. The device of any one of claim 7-14, wherein said inner surface opposite said arched convex outer surface of each said plate has small points thereon for anchoring said plate on a vertebral body.

16. The device of any one of claim 7, 8, 9 and 11, wherein said means for anchoring said plates comprises two bores extending through each said plate and screws to be received in said bores, said bores being located in the vicinity of the ends of said plates, and said means for locking said first rod in said plates comprising a tapped hole in each said plate connecting said arched outer surface thereof to said opening of said boss and a screw adapted to be screwed into said tapped hole.

17. The device of any one of claims 7, 8, 9 and 11, wherein said means for anchoring said plates comprises two bores extending through each said plate and screws to be received in said bores, said bores being located in the vicinity of the ends of said plates, and one of said bores is a lateral or posterior bore, each said plate having a sufficient length for said lateral or posterior bore to be able to fix said second rod to said plate through said lateral or posterior bore with said means for fixing said second rod.

18. The osteosynthesis device of any one of claims 7, 8, 9 and 11, wherein said opening of said boss is a channel in said boss open on said arched outer surface for receiving said second rod, said means for locking said first rod comprising tappings on the edges of said channel and a bolt adapted to be screwed into said tappings.

* * * * *